(12) United States Patent
Norton et al.

(10) Patent No.: US 10,681,922 B2
(45) Date of Patent: Jun. 16, 2020

(54) METHODS OF ENHANCING THE GASTROINTESTINAL HEALTH OF A COMPANION ANIMAL

(71) Applicant: Mars, Incorporated, McLean, VA (US)

(72) Inventors: Sharon Ann Norton, Dayton, OH (US); Gary Gregory Goldy, Lewisburg, OH (US)

(73) Assignee: Mars, Incorporated, McLean, VA (US)

( * ) Notice: Subject to any disclaimer, the term of this patent is extended or adjusted under 35 U.S.C. 154(b) by 447 days.

(21) Appl. No.: 15/294,503

(22) Filed: Oct. 14, 2016

(65) Prior Publication Data

US 2017/0027191 A1 Feb. 2, 2017

Related U.S. Application Data

(62) Division of application No. 10/725,248, filed on Dec. 1, 2003.

(51) Int. Cl.
*A23K 10/30* (2016.01)
*A23K 20/163* (2016.01)
*A23K 50/40* (2016.01)
*A23K 20/147* (2016.01)

(52) U.S. Cl.
CPC ............ *A23K 10/30* (2016.05); *A23K 20/147* (2016.05); *A23K 20/163* (2016.05); *A23K 50/40* (2016.05)

(58) Field of Classification Search
CPC ...................................................... A23K 10/30
See application file for complete search history.

(56) References Cited

U.S. PATENT DOCUMENTS

| | | |
|---|---|---|
| 3,119,691 A | 1/1964 | Ludington et al. |
| 3,908,025 A | 9/1975 | Miller et al. |
| 4,020,187 A | 4/1977 | McCulloch |
| 4,241,093 A * | 12/1980 | Farag ........................ A23L 19/10 426/258 |
| 4,551,351 A | 11/1985 | Kawasaki et al. |
| 4,613,377 A | 9/1986 | Yamazaki et al. |
| 4,734,402 A | 3/1988 | Hashimoto et al. |
| 4,746,528 A | 5/1988 | Prest et al. |
| 4,865,852 A | 9/1989 | Tamatani et al. |
| 4,927,811 A | 5/1990 | Quarles |
| 4,987,124 A | 1/1991 | Speights |
| 5,085,883 A | 2/1992 | Garleb et al. |
| 5,116,629 A | 5/1992 | Schroeder et al. |
| 5,118,503 A | 6/1992 | Sawai et al. |
| 5,221,552 A | 6/1993 | Masuda et al. |
| 5,294,458 A | 3/1994 | Fujimori |
| 5,422,136 A | 6/1995 | Fuisz |
| 5,605,114 A | 2/1997 | Peltenburg et al. |
| 5,616,569 A * | 4/1997 | Reinhart ................ A23K 10/37 426/630 |
| 5,709,888 A | 1/1998 | Gil et al. |
| 5,744,134 A | 4/1998 | Paul |
| 5,776,524 A | 7/1998 | Reinhart |
| 5,840,361 A | 11/1998 | Theuer et al. |
| 5,952,033 A | 9/1999 | Anantharaman et al. |
| 5,958,898 A | 9/1999 | Hayek et al. |
| 5,965,175 A | 10/1999 | Reinhart et al. |
| 5,968,569 A | 10/1999 | Cavadini et al. |
| 6,039,952 A | 3/2000 | Sunvold et al. |
| 6,093,418 A | 7/2000 | Sunvold et al. |
| 6,117,872 A | 9/2000 | Maxwell et al. |
| 6,156,355 A | 12/2000 | Shields et al. |
| 6,180,131 B1 | 1/2001 | Sunvold et al. |
| 6,248,390 B1 | 6/2001 | Stillman |
| 6,306,442 B1 | 10/2001 | Sunvold et al. |
| 6,312,746 B2 | 11/2001 | Paluch |
| 6,383,534 B1 | 5/2002 | Dyrr et al. |
| 6,391,375 B1 * | 5/2002 | Fone ...................... A23K 10/30 426/635 |

(Continued)

FOREIGN PATENT DOCUMENTS

| | | |
|---|---|---|
| CH | 570117 A5 | 12/1975 |
| DE | 2403203 A1 | 7/1975 |

(Continued)

OTHER PUBLICATIONS

"Mixture definition", Retrieved from the Internet on Feb. 18, 2015, Retrieved from http://dictionary.reference.com/browse/mixture, 3 page.
"Definition of Companion", Access at http://dictionary.reference.com/search?q=companion&r=66, Jan. 6, 2006, 1 pg.
"Nutrient Requirements of Dogs and Cats, Ch. 4, Carbohydrates and Fiber", National Research Council of The National Academies, ISBN: 0-309-09062-8, 2003, pp. 55-90.
"Official Methods of Analysis", AOAC, 1990, Animal feed, pp. 69-90.
"Wikipedia, Food", Accessed: Jan. 6, 2006 at http://en.wikipedia.org/wiki/Food, 1 pg.
Briggs, "Feeding Beet Pulp", American Association of Equine Practitioners, Jun. 18, 2002 (Retrieved from the internet on: Dec. 9, 2012) Retrieved from http://www.aaep.org/health_articles_view.php?id=111, 2 pgs.
Campbell, et al., "Selected Fructooligosaccharide (1-Kestose, Nystose, and 1-beta-fructofuranosylnystose) Composition of Foods and Feeds", Journal of Agricultural Food Chemicstry, 1997, vol. 45., pp. 3076-3082.

(Continued)

*Primary Examiner* — Amy L Clark
(74) *Attorney, Agent, or Firm* — Mars, Incorporated

(57) ABSTRACT

Disclosed herein are methods for enhancing the gastrointestinal health of a companion animal, comprising orally administering to the companion animal a composition comprising at least about 0.25% of fermentable fiber by weight of the composition. Further disclosed herein are methods of improving the fecal odor of the feces of a companion animal, comprising orally administering to the companion animal a composition comprising at least about 0.25% of fermentable fiber by weight of the composition. In some embodiments of these methods, the fermentable fiber comprises a fiber selected from beet pulp, gum Arabic, gum talha, psyllium, rice bran, carob bean gum, citrus pulp, pectin, fructooligosaccharide, mannanoligofructose, soy fiber, arabinogalactan, galactooligosaccharide, arabinoxylan, a short chain oligofructose, and a mixture thereof.

17 Claims, No Drawings

(56) References Cited

U.S. PATENT DOCUMENTS

| | | |
|---|---|---|
| 6,468,525 B1 | 10/2002 | Watson et al. |
| 6,475,512 B1 | 11/2002 | Sunvold et al. |
| 6,500,805 B2 | 12/2002 | Van Loo et al. |
| RE38,112 E | 5/2003 | Sunvold et al. |
| 6,596,332 B1 | 7/2003 | Anantharaman et al. |
| 6,656,512 B1 | 12/2003 | Fone et al. |
| 6,669,975 B1 | 12/2003 | Abene et al. |
| 6,818,225 B2 | 11/2004 | Sunvold et al. |
| 6,991,812 B2 | 1/2006 | Suzuki et al. |
| 7,101,553 B2 | 9/2006 | Haschke et al. |
| 7,189,390 B2 | 3/2007 | Zink et al. |
| 7,211,280 B1 | 5/2007 | Young et al. |
| 7,608,291 B2 | 10/2009 | Ballion et al. |
| 7,812,004 B2 | 10/2010 | Frippiat et al. |
| 8,092,608 B2 | 1/2012 | Rochat et al. |
| 2002/0132780 A1 | 9/2002 | Heisey et al. |
| 2003/0040492 A1 | 2/2003 | Haschke et al. |
| 2003/0099759 A1 | 5/2003 | Cheuk et al. |
| 2003/0138547 A1 | 7/2003 | Bui et al. |
| 2003/0194423 A1 | 10/2003 | Torney et al. |
| 2003/0194478 A1 | 10/2003 | Davenport et al. |
| 2005/0118299 A1 | 6/2005 | Vickers et al. |
| 2005/0119222 A1 | 6/2005 | Norton et al. |
| 2005/0123643 A1 | 6/2005 | Cupp et al. |
| 2005/0281910 A1 | 12/2005 | Schiffrin et al. |
| 2010/0150870 A1 | 6/2010 | Young et al. |

FOREIGN PATENT DOCUMENTS

| | | |
|---|---|---|
| DE | 4304394 A1 | 9/1993 |
| EP | 0058651 A1 | 8/1982 |
| EP | 0674842 A1 | 10/1995 |
| JP | 61135551 | 6/1986 |
| JP | S63309147 A | 12/1988 |
| JP | H01252257 A | 10/1989 |
| JP | 03061452 | 3/1991 |
| JP | H10416163 | 1/1992 |
| JP | 05219896 | 8/1993 |
| RU | 2142720 | 12/1999 |
| WO | 02096211 | 12/2002 |
| WO | 02100188 | 12/2002 |

OTHER PUBLICATIONS

Cashman, "Prebiotics and Calcium Bioavailability", Horizon Scientific Press, Microbiol. 2003, 4:21-32.

Chandra, et al., "The Addition of Neosugar to Oral Electrolyte Solutions (OES) for Treatment of Acute Diarrhea", FASEB Journal, Fed. of American Society for Experimental Biology, Bethesda, MD, US, vol. 9, No. 3, 1995, p. A368.

Flickinger, et al., "Nutrient Digestibilities, Microbial Populations, and Protein Carbolites as Affected by Fructan Supplementation of Dog Diets", J.Anim.Sci.2003, 81:pp. 2008-2018.

Foster, et al., "Benefits of Beet Pulp in Pet Foods, Beet Pulp: Its Benefits in Pet Food", Veterinary & Aquatic Services Department, Accessed at http://web.archive.org/web/*/http://www.peteducation.com/article.cfm?cls=1&cat+1399&articleid=2705, Jan. 5, 2006, 3 pgs.

Grant, et al., "Development of Buffer Systems for pH Control and Evaluation of pH Effects on Fiber Digestion In Vitro", J. Dairy Sci., vol. 75, Issue 6, Jun. 1992, pp. 1581-1587.

Grieshop, et al., "Gastrointestinal and Immunological Responses of Senior Dogs to Chicoroy and Mannanoligosaccharides", FASEB Journal, vol. 17, No. 4-5, Mar. 2003 XP002324194, Abstract No. 202.5 ( 1 pg).

Griffin, et al., "Enriched Chicory Inulin Increases Calcium Absorption Mainly In Girls With Lower Calcium Absorption", Nutrition Research, 23 (2003) pp. 901-909.

Hogarth, et al., "Ion Chromatographic Determination of Three Fructooligosaccharide Oligomers in Prepared and Preserved Foods", Journal of Agricultural and Food Chemistry, vol. 48, 2000 pp. 5326-5330.

Houdijk, et al., Livestock Production Science, 73, 2002 p. 175-184.

Howard, et al., "Source of Dietary Fiber Fed to Dogs Affects Nitrogen and Energy Metabolism and Intestinal Microflora Populations", Nutrition Research, 2000, 20(10), p. 1473-1484.

Hussein, et al., "Petfood Applications of Inulin and Oligofructose", Journal of Nutrition, vol. 129, 1999, pp. 1454-1456.

Hussein, et al., "Selected Fructooligosaccharide Composition of Pet-Food Ingredients", Components of Pet Food, American Society for Nutritional Sciences, The Journal of Nutrition, 128, pp. 2803S-2805S, 1998.

Kaplan, et al., "Fermentation of Fructooligosaccharides by Lactic Acid Bacteria and Bifidobacteria", Applied and Environmental Microbiology, Jun. 2000, vol. 66(6): 2682-2684.

L'Homme, et al., "Effect of Food Processing on the Degradation of Fructoligosaccharides in Fruit", Food Chemistry, vol. 82 (2003), p. 533-537.

Mineo, et al., "Nutrient Interactions and Toxicity Research Communication", The Journal of Nutrition, Dec. 2001, 131, 12: Research Library, pp. 3243-3246.

Morohashi, et al., "Nutrient Requirements and Interactions Research Communication", The Journal of Nutrition, Oct. 1998, 128, 10; Research Library, pp. 1815-1818.

Ohta, et al., "Nutrient Interactions and Toxicity", The Journal of Nutrition, Jul. 2002, 132, 7: Research Library, pp. 2048-2054.

Ohta, et al., "Prevention of Coprophagy Modifies Magnesium Absorption In Rats Fed with Fructo-Oligosaccharides", British Journal of Nutrition, vol. 75, No. 5, 1996, pp. 775-784, Abstract XP002324183.

Oli, et al., "Influence of Fructooligosaccharide (Neosugar) in Oral Electrolyte Solutions (OES) for Treatment of Secretory Diarrhea", Abstracts of the General Meeting of the American Society for Microbiology, the Society, Washington, DC, US, vol. 95, 1995, p. 205.

Oyarzabal, et al., "Applicantion of Direct-Fed Microbial Bacteria and Fructooligosaccharides for *Salmonella* Control in Broilers During Feed Withdrawal", Dept. of Poultry Science, 1996, vol. 75 p. 186-19.

Patil, et al., "Supplementation of Soluble Fiber to Wet Cat Food Affects Fecal Micrflora of Cats", FASEB Journal vol. 6, No. 4, Mar. 20, 2002 p. A654, Abstract XP002324182.

Propst, et al., "A Dose-Response Experiment Evaluating the Effects of Oligofructose and Inulin on Nutrient Digestibility, Stool Quality, and Fecal Protein Catabolites in Healthy Adult Dogs", J. Animal Science, vol. 81, 2003 pp. 3057-3066.

Richardson, et al., "Developmental Orthopedic Disease of Dogs", Small Animal Clinical Nutrition, 4th Edition (2000), Ch. 17, pp. 505-521.

Roberfroid, "Chicory Fructooligosaccharides and the Gastrointestinal Tract", Nutrition, 16, Nos. 7/8, 2000 677-679.

Sparkes, et al., "Bacterial flora in the duodenum of healthy cats, and effect of dietary supplmentation with fructooligosaccharides", American Journal of Veterinary Research, AJVR 59(4), 1998, 431-435.

Strickling, et al., "Evaluation of Oliogosaccharide Addition to Dog Diets: Influences on Nutrient Digestion and Microbial Populations", Animal Feed Science and Technology, vol. 86, 2000 pp. 205-219.

Sunvold, et al., "Dietary Fiber for Dogs: IV. In Vitro Fermentation of Selected Fiber Sources by Dog Fecal Inoculum and In Vivo Digestion and Metabolism of Fiber-Supplemented Diets", J. Anim. Sci, vol. 73, 1995, 1099-1109.

Sunvold, et al., "In Vitro Fermentation of Cellulose, Beet Pulp, Citrus Pulp, and Citrus Pectin Using Fecal Inoculum from Cats, Dogs, Horses, Humans, and Pigs and Ruminal Fluid from Cattle", J. Anim. Sci. 1995, 73:3639-3648.

Sunvold, et al., "In Vitro Fermentation of Selected Fibrous Substrates by Dog and Cat Fecal Inoculum: Influence of Diet Composition on Substrate Organic Matter Disappearance and Short-Chain Fatty Acid Production", Journal of Animal Science, vol. 73, No. 4, 1995 pp. 1110-1122.

Swanson, et al., "Supplemental Fructooligosaccharides and Mannanoligosaccharides Influence Immune Function, Illeal and Total Tract Nutrient Digestibilities, Microbial Poplulations and Concen-

(56) References Cited

OTHER PUBLICATIONS trations of Protein Catabolites in the Large Bowel of Dogs", American Society for Nutritional Sciences, vol. 132, 2002, pp. 980-989.
Tahiri, et al., "Effect of short-chain fructooligosaccharides on Intestinal Calcium Absorption and Calcium Status in Postmenopausal Women: A Stable-Isotope Study", Am. J. Clin. Nutr., 2003, 77, pp. 449-457.
Takahara, et al., "Nutrient Metabolism—Research Communication", The Journal of Nutrition, Jul. 2000, 130 7: Research Library, pp. 1792-1795.
Takasaki, et al., "Dietary Short-Chain Fructooligosaccharides Increase Calbindin-D9k Levels Only in the Large Intestine in Rats Independent of Dietary Calcium Deficiency or Serum 1,25 Dihydroxy Vitamin D Levels", Int. J. Vitam. Nutr. Res., 70(5), 2000, pp. 206-213.
Vickers, et al., "Comparison of Fermentation of Selected Fructooligosaccharides and Other Fiber Substrates by Canine Colonic Microflora", AJVR, vol. 62, No. 4, Apr. 2001, 609-615.
Willard, et al., "Effects of Dietary Supplementation of Fructooligosaccharides on Small Intestinal Bacterial Overgrowth in Dogs", Am. J. Vet Res., vol. 55, No. 5, May 1994, pp. 654-659.
Zentek, et al., "Dietary Effects on Bifidobacteria and Clostridium Perfringens in the Canine Intestinal Trace", Journal of Animal Physiology and Animal Nutrition, vol. 87, Nov. 2003, pp. 397-407, XP002324180.
Ziegler, et al., "Present Knowledge in Nutrition", International Life Sciences Institute, 7th Edition, 1996 pp. 245-255.
"A Balanced Diet", Waltham Book of Dog and Cal Nutrition, Ed. ATB, Edney, Chapter by A. Rainbird, pp. 57-74, Pergamon Press, Oxford, 1988.
"Chicory Pulp for Canines", Encore Technologies Specification; Dried Chicory Pulp, Aug. 7, 1998, 5 pgs.
"Comparative Digestion Physiology", http://www.avs.uidaho.edu/avs305/comparative%20digestion.htm, retrieved from the Internet on Jan. 9, 2019, 1 pg.
"Dried Chicory Pulp", Cigarant, H2796NL00, 2 pgs, Aug. 22, 2006, from http://content.consun.nl/Suikerunie/nl/66_Gedr-Cigaratnt.htm.
Aldrich, et al., "The Effects of Endophyte-infected Tall Fescu Consumption and Use of a Dopamine Antagonist on Intake, Digestibility, Body Temperature, and Blood Constituents in Sheep", Journal of Animal Science, vol. 71, Issue 1, Jan. 1, 1993, pp. 158-163 (Abstract Only), 4 pgs.
Barnard, et al., "The Apparent Reversal of a Wasting Syndrome by Nutritional Intervention in Saguinus Mystax", Laboratory Animal Science, Jun. 1988, vol. 38(3): 282-288, Abstract only, 2 pgs.
Bourquin, et al., "Fermentation of Dietary Fibre by Human Colonic Bacteria: disappearance of, short-chain fatty acid production from, and potential water-holding capacity of, various substrates.", Scandinavian Journal of Gastroenterology, Mar. 1993, vol. 28(3): 249-255 (Abstract only, 1 pg).
Diez, et al., ""Etude des fibres almentaires chez le chien: présentation des résultats de 7 essais expérimentaux" (Study of dietary fiber in dogs: presentation of the results of 7 experimental trials)", Annales Des Medecine Veterinaire, Jan. 1, 1998, vol. 142, Nr:3, pp. 185-198,200/201(Abstract, 3 pgs).
Dimski, et al., "Dietary Fiber in Small Animal Therapeutics", Timely Topics in Nutrition, JAVMA, vol. 199, No. 9, Nov. 1991, 5 pgs.
Edwards, "The Mechanisms of Action of Dietary Fibre in Promoting Colonic Propulsion", Scandinavian Journal of Gastroenterology, vol. 22, Suppl. 129, p. 97-99, 1987 (Publ online Jul. 2009).

Fahey, et al., "Dietary fiber for dogs: I. Effects of Graded Levels of Dietary Beet Pulp on Nutrient Intake, Digestibility, Metabolizable Energy and Digesta Mean Retention Time", J. Anim. Sci., Dec. 1990, 68(12):4221-4228.
Fahey, et al., "Dietary Fiber for Dogs: II. Iso-Total Dietary Fiber (TDF) Additions of Divergent Fiber Sources to Dog Diets and Their Effects on Nutrient Intake, Digestibility, Metabolizable Energy and Digesta Mean Retention Time", Journal of Animal Science, vol. 68:4229-4235, Dec. 1990 (Abstract Only, 2 pgs).
Fahey, et al., "Dietary Fiber for Dogs: III. Effects of Beet Pulp and Oat Fiber Additions to Dog Diets on Nutrient Intake, Digestibility, Metabolizable Energy, and Digesta Mean Retention Time", Journal of Animal Science, vol. 70:1169-1174, 1992 (Abstract only, 4 pgs).
Gedek, "Regulation of the Intestinal Flora by Food", Zentralbl Hyg. Umweltmed. Mar. 1991; 191(2-3):277-301, Abstract only, 2 pgs.
Gibson, "Dietary Modulation of the Human Colonic Microbiota: Introducing the Concept of Prebiotics", American Institute of Nutrition Jun. 1995, Critical Review 0022-3166/95; p. 1401-1412.
Glawischnig, "Antibiotic-free Weaning of Piglets", Dtsch Tierarztl Wochenschr. Jan. 1990;97(1):48-51. Abstract only, 1pg.
Hallman, et al., "Colonic Mucosal Tissue Energetics and Electrolyte Transport in Dogs Fed Cellulose, Beet Pulp or Pectin/Gum Arabic as Their Primary Fiber Source", Nutrition Research, vol. 16, No. 2, p. 303-316, Feb. 1996.
Klop, et al., "Cigarant as a substitution for concentrates in grass silage rations for dairy cattle", Animal Sciences Group, 2003, 1 pg Abstract.
Kritchevsky, "Dietary Fiber", Annual Review of Nutrition,vol. 8:301-328 (Volume publication date Jul. 1988).
Merchen, et al., "Researchers seek best way to assess fiber in dog food", Feedstuffs, May 14, 1990, No. 49, 5 pgs.
Mortensen, et al., "Short-chain Fatty Acids in the Human Colon: Relation to Gastrointestinal Health & Disease", Scandinavian Journal of Gastroenterol, 31 Suppl. 216: 132-48, 1996 (Published online Jul. 8, 2009) (Abstract only, 2 pgs).
Pethick, et al., "The Effects of *Arctotheca calendula* (capeweed) on Digestive Function of Sheep", Australian Veterinary Journal, vol. 68, Issue 11, Nov. 1991, Abstract only, 2 pgs.
Reinhart, et al., "Source of Dietary Fiber and its Effects on Colonic Microstructre, Function and Histophathology of Beagle Dogs", The Journal of Nutrition, vol. 124, Issue suppl. 12, Dec. 1, 1994, pp. 2701S-2703S, (Expanded Abstract Only, 1 pg).
Sunvold, et al., "Fermentability of Selected Fibrous Substrates by Cat Fecal Microflora", Journal of Nutrition vol. 124:2721S-2722S, Dec. 1994.
Sunvold, et al., "Fermentability of Selected Fibrous Substrates by Dog Fecal Microflora as Influenced by Diet", Journal of Nutrition, vol. 124:2719S-2720S, Dec. 1994.
Swanson, et al., "Fruit and Vegetable Fiber Fermentation by Gut Microflora from Canines", Journal of Animal Science, vol. 79: 919-926, Apr. 2001, 8 pgs.
Wang, et al., "Effects of the in vitro fermentation of oligofructose and inulin by bacteria growing in the human large intestine", Journal of Applied Bacteriology, May 1993; #75, p. 373-380.
Zentek, "Cellulose, pectins and guar gum as fiber sources in canin diets", Journal of Animal Physiology and Animal Nutrition, vol. 75(Dec. 1996), p. 36-45 (Abstract, 4 pgs).
Hallman, et al., "Cellulose, Beet Pulp, and Pectin/Gum Arabic Effects on Canine Colonic Microstructure and Histopathology", Veterinary Clinical Nutrition, vol. 2, No. 4, 1995, p. 137-142.
Munchow, et al., "An Examination of the Use of Partly Hydrolysed Straw Meal in Feeding Weaned Piglets", Arch. Anim. Nutr., Arch. Tieremahr, 38(5), p. 375-385 & 359-373, Sep. 14, 1987.
Sunvold, et al., "Dietary Fiber for Dogs: III. Effects of Beet Pulp and Oat Fiber Additions to Dog Diets on Nutrient Intake, Digestibility, Megabolizable Energy, and Digest Mean Retention Time", J. Anim. Sci. vol. 70, 1169-1174, Nov. 6, 1991.
Sunvold, et al., "Fermentability of Various Fibrous Substrates by Canine Fecal Microflora", The FASEB Journal, Mar. 28-Apr. 1, 1993, p. A740.

* cited by examiner

METHODS OF ENHANCING THE GASTROINTESTINAL HEALTH OF A COMPANION ANIMAL

CROSS REFERENCE TO PRIORITY APPLICATION

This application is a divisional of U.S. application Ser. No. 10/725,248, filed Dec. 1, 2003 (pending), which is incorporated herein in its entirety.

FIELD

The present disclosure is directed to compositions comprising a fermentable fiber, wherein the compositions are adapted for use by a companion animal. The disclosure is further directed to kits comprising such compositions as well as methods of using the compositions and/or the kits.

BACKGROUND

Gastrointestinal health is a consistent concern among guardians of companion animals, including breeders and veterinarians. Stomach upset, refusal to ingest food, diarrhea, and the like can be distressing for the guardian and companion animal alike. Many currently available pet foods contain components which serve to enhance gastrointestinal health, however, it is recognized that not all guardians of companion animals choose to make these higher quality foods available to their companion animals Rather, many guardians are attracted to purchasing lower quality foods with the mindset that their companion animal will more readily enjoy the taste or appearance of such food.

Still further, many traditional forms of companion animal food are not completely consumed by the companion animal. As such, the animal may be lacking in basic nutritional requirements.

It is therefore necessary to seek developments which encourage guardians of companion animals to provide supplements to the ordinary dietetic intake of the companion animal Most recently, supplements such as gravies have been introduced to the marketplace. Many such supplements provide a wide variety of vitamins and minerals, as well as palatability aids such as animal meats and fats.

The present inventors provide herein compositions which are useful for enhancing the gastrointestinal health of companion animals. Such compositions may be readily accepted by guardians of companion animals which have not been previously fed high quality companion animal foods, or those which do utilize such high quality foods while still searching for added health benefit for their animal.

SUMMARY

The present disclosure is directed to compositions, kits, and methods which are adapted for use by companion animals. In one embodiment of the present disclosure, compositions are provided which comprise at least about 0.25% of total fermentable fiber, by weight of the composition, wherein the composition is a liquid. In another embodiment herein, compositions are provided which comprise a beet pulp or a short chain oligofructose comprising one or more components selected from the group consisting of 1-kestose, nystose, and 1F-beta-fructofuranosylnystose, wherein the composition is a liquid which is adapted for use by a companion animal.

Kits comprising such compositions along with information that such compositions are adapted for use by a companion animal, or other information, are also provided. Even further, the present disclosure provides methods of enhancing the gastrointestinal health or improving the fecal odor of the feces of the of the companion animal comprising orally administering the composition to the companion animal.

DETAILED DESCRIPTION

Various documents including, for example, publications and patents, are recited throughout this disclosure. All such documents are hereby incorporated by reference. The citation of any given document is not to be construed as an admission that it is prior art with respect to the present disclosure.

All percentages and ratios are calculated by weight unless otherwise indicated. All percentages and ratios are calculated based on the total composition unless otherwise indicated.

Referenced herein are trade names for components including various ingredients utilized in the present disclosure. The inventors herein do not intend to be limited by materials under a certain trade name. Equivalent materials (e.g., those obtained from a different source under a different name or reference number) to those referenced by trade name may be substituted and utilized in the descriptions herein.

In the description, various embodiments and/or individual features are disclosed. As will be apparent to the ordinarily skilled practitioner, all combinations of such embodiments and features are possible and can result in preferred executions of the inventions of the present disclosure.

The compositions herein may comprise, consist essentially of, or consist of any of the features or embodiments as described herein.

While various embodiments and individual features of the present disclosure have been illustrated and described, various other changes and modifications can be made without departing from the spirit and scope of the disclosure. As will also be apparent, all combinations of the embodiments and features taught in the foregoing disclosure are possible and can result in preferred embodiments.

The present disclosure is directed to compositions, kits, and methods which are adapted for use by companion animals. As used herein, "companion animal" means a domestic animal. Preferably, "companion animal" means a domestic dog, cat, rabbit, ferret, horse, cow, or the like. More preferably, "companion animal" means a domestic dog or cat, particularly a domestic dog.

In one embodiment, compositions are provided which comprise fermentable fiber, wherein the composition is a liquid. Kits comprising such compositions along with information that such compositions are adapted for use by the companion animal are also provided. Even further, the present disclosure provides methods of enhancing the gastrointestinal health of the companion animal comprising orally administering the composition to the companion animal.

The compositions herein are adapted for use by a companion animal. In this respect, as will be well-understood by the ordinarily skilled artisan, the primary use of the compositions described herein is for companion animal use and the compositions are therefore formulated as such.

As described herein, in one embodiment, compositions are provided which comprise at least about 0.25% of total fermentable fiber, by weight of the composition, wherein the composition is a liquid. In another embodiment herein, compositions are provided which comprise a short chain oligofructose comprising 1-kestose, nystose, and 1F-beta-fructofuranosylnystose, wherein the composition is a liquid. The compositions are adapted for use by a companion animal.

Fermentable fibers provide an important role in the gastrointestinal health of companion animals. High quality companion animal foods, such as certain foods commercially marketed as IAMS or EUKANUBA foods (The Iams Company, Dayton, Ohio, U.S.A.) provide fermentable fibers as a component of daily kibble diet. However, many commercially available companion animal foods are devoid of such components, which can compromise the gastrointestinal health, or optimization of the gastrointestinal health, of the companion animal. Even further, commercially available gravies or other aqueous supplements fail to provide such fermentable fibers, particularly at meaningful levels for efficacious treatment of the companion animal. As such, gravies which are provided to supplement the nutritional benefits of daily animal feed fail to provide the important elements for sound gastrointestinal health. The present inventors have advantageously discovered that the compositions adapted for use by companion animals are particularly suited for supplementing these needs. As an example, the present compositions may be used to supplement diets which are already of high quality, or to supplement compromised diets.

Fermentable fibers are well-known in the art. The fermentable fiber may be any fiber source which intestinal bacteria present in the animal can ferment to produce short chain fatty acids or other metabolic components. Non-limiting examples of such fermentable fibers include beet pulp (from sugar beet), gum arabic, gum talha, psyllium, rice bran, carob bean gum, citrus pulp, pectin, fructooligosaccharide, mannanoligofructose, soy fiber, arabinogalactan, galactooligosaccharide, arabinoxylan, and mixtures thereof.

In general, fermentable fibers are not digested by mammals but may be metabolized by intestinal bacterial species, such as *Bifidobacterium*. However, not all intestinal bacteria can metabolize fermentable fiber. In particular, bacteria such as *Salmonella*, *E. coli* and *Clostridia* are unable to process such fiber to any meaningful degree. This preferential digestibility, which is applicable for fermentable fiber as a class, can be used to improve the overall bacterial flora in the small intestine of the companion animal. Because fermentable fibers will only feed "good" bacteria such as *Lactobacillus* and *Bifidobacterium*, the amounts of harmful bacteria such as *Salmonella*, *E. coli* and *Clostridia* may decrease due to a reduction in food resources. Therefore, by providing a preferred food source for beneficial bacterial species, a diet supplemented with fermentable fiber can increase "good" intestinal bacteria while reducing the amount of "bad" bacteria.

Beet pulp and fructooligosaccharide, particularly short chain oligofructose, are particularly preferred fermentable fibers for use herein. As an example, fructooliogosaccharides are naturally occurring compounds which can be found in a variety of fruits or vegetables including banana, barley, garlic, honey, onion, rye, brown sugar, tomato, asparagus, artichoke, wheat, yacon, or chicory. Fructooligosaccharide may for example be provided as chicory root, as a long chain oligofructose (e.g., inulin), or as short chain oligofructose. Particularly useful herein are fructooligosaccharide comprising at least one of 1-kestose (abbreviated as $GF_2$), nystose ($GF_3$), and 1F-beta-fructofuranosylnystose ($GF_4$). While fructooligosaccharides can be extracted from plants such as those mentioned herein, they can also be formed artificially by adding one, two, or three fructose units to a sucrose molecule by a B-(2-1)-glycosidic linkage of the fructose unit(s) to the fructose unit of sucrose. As an example, fructooligosaccharides are commercially available under the tradename NUTRAFLORA from Golden Technologies Company, Incorporated (which is a short chain oligofructose comprising 1-kestose, nystose, and 1F-beta-fructofuranosylnystose. As another example, a mixture of short chain fructooligosaccharide and inulin can be PRE-BIO1 or a mixture of commercially available RAFTILOSE and RAFTILINE.

The fructooligosaccharide may be a short chain oligofructose, which will be well-known to those of ordinary skill in the art. Particularly useful herein are short chain oligofructose comprising 1-kestose (abbreviated as $GF_2$), nystose ($GF_3$), and 1F-beta-fructofuranosylnystose ($GF_4$). In a preferred embodiment, the short chain oligofructose comprises from about 25% to about 45% 1-kestose, from about 25% to about 45% nystose, and from about 1% to about 20% 1F-beta-fructofuranosylnystose, by weight of the short chain oligofructose, alternatively from about 30% to about 40% 1-kestose, from about 50% to about 60% nystose, and from about 5% to about 15% 1F-beta-fructofuranosylnystose, by weight of the short chain oligofructose. As an example, short chain oligofructose is commercially available under the tradename NUTRAFLORA from Golden Technologies Company, Incorporated (which is a short chain oligofructose comprising about 35% 1-kestose, 55% nystose, and 10% 1F-beta-fructofuranosylnystose, all by weight of the short chain oligofructose).

In an embodiment herein, the fermentable fibers may display certain organic matter disappearance percentages. In this optional embodiment, the fermentable fibers may have an organic matter disappearance (OMD) of from about 15% to about 60% when fermented by fecal bacteria in vitro over a 24 hour period. That is, from about 15% to about 50% of the total organic matter originally present is fermented and converted by the fecal bacteria. The organic matter disappearance of the fibers is alternatively from about 20% to about 50%, alternatively from about 30% to about 40%.

Thus, in vitro OMD percentage may be calculated as follows:

$$(1-((\text{OM residue}-\text{OM blank})/\text{original OM}))\times 100$$

where OM residue is the organic matter recovered after 24 hours of fermentation, OM blank is the organic matter recovered in corresponding blank tubes (i.e., tubes containing medium and diluted feces, but no substrate), and original OM is that organic matter placed into the tube prior to fermentation. Additional details of the procedure are found in Sunvold et al., J. Anim. Sci., Vol. 73, pp. 1099-1109 (1995).

In one embodiment herein, the compositions comprise at least about 0.25% total fermentable fiber, by weight of the composition. By "total fermentable fiber" it is meant that the referenced level is determined by adding the relative amounts of each fermentable fiber present in the composition. For example, wherein a composition comprises 1% fructooligosaccharide and 0.5% beet pulp, by weight of the composition, and no other fermentable fiber, the composition comprises 1.5% total fermentable fiber, by weight of the composition. Alternatively, the present compositions comprise at least about 0.5% total fermentable fiber, at least about 1% total fermentable fiber, at least about 2% total fermentable fiber, alternatively from about 1% to about 20% total fermentable fiber, alternatively from about 1% to about 10% total fermentable fiber, alternatively from about 2% to about 10% total fermentable fiber, or alternatively from about 3% to about 8% total fermentable fiber, all by weight of the composition.

Alternatively or additionally, wherein short chain oligofructose is utilized, it has been surprisingly discovered that, optionally, at least about 0.05% of the short chain oligofructose may be utilized, alternatively from about 0.1% to about 20%, alternatively from about 0.1% to about 10%, alternatively from about 0.1% to about 8%, alternatively from about 0.15% to about 5%, all by weight of the composition.

The compositions herein are liquids; as used herein, the term "liquid" is as will be commonly understood in the art, with the understanding that the composition may contain solid particulates or other solid matter while still maintaining the overall liquid character of the composition. Liquids are typically flowable at ambient temperature. The compositions are typically intended for use by companion animals as a supplement to ordinary dietetic needs. As such, these compositions are advantageously provided as drinking waters, gravies, or other supplements. Drinking waters may be fully or partially substituted for ordinary drinking water provided to the companion animal, or may even be in contact with, or admixed with, companion animal food. Gravies, as described herein, are broadly defined. Gravies may be any gravy, topping, sauce, or other liquid mixture. Gravies may have a viscosity which is greater than distilled water at ambient temperature. Gravies may be orally administered directly to the companion animal, but are advantageously contacted or admixed with food prior to oral administration.

The compositions may optionally comprise at least about 50% water, by weight of the composition. In alternative embodiments, the compositions comprise at least about 60% water, at least about 70% water, at least about 80% water, from about 50% to about 99% water, from about 60% to about 97% water, from about 70% to about 95% water, or from about 75% to about 90% water, all by weight of the composition. The water included at these levels includes all added water and any water present in combination components, for example, broths.

Optional Components of the Present Compositions

The compositions herein may comprise additional optional components to enhance, for example, their performance in providing gastrointestinal health, other health benefits, a desirable nutritional profile, and/or organoleptic properties. Such optional components may be dispersed, solubilized, or otherwise mixed into the present compositions. Non-limiting examples of optional components suitable for use herein are given below.

Meats, Broths, and Fats

Any of a variety of animal meats, broths, or fats may be utilized as components of the present compositions. For example, animal meats such as chicken, pork, beef, veal, fish, and the like may be utilized. Advantageously, such meats are in particle or chunk form, such that the composition maintains an overall liquid form, such as spray-dried animal meats. Broths and fats of any animal meats may be used.

Flavors

The meats, broths, or fats mentioned herein may also be utilized as a flavor to enhance palatability of the composition. Optionally, one or more other flavors may additionally or alternatively be utilized. Any natural or synthetic flavor can be used in the present invention.

Flavors may be those which are meat flavors, for example, by utilizing a meat source or a flavor which simulates a meat flavor. For example, yeast may be utilized to simulate chicken flavor as desired. Other natural or synthetic meat extracts may be used. Moreover, as another example, vegetable flavors or flavors which simulate the properties of vegetable flavors may be utilized.

The flavor agent can also comprise a blend of various flavors. If desired, the flavor in the flavoring agent may be formed into emulsion droplets which are then dispersed in the composition. Typically the flavoring agents are conventionally available as concentrates or extracts or in the form of synthetically produced flavoring esters, alcohols, aldehydes, terpenes, sesquiterpenes, and the like.

pH

The present compositions may have any pH, provided that the composition is adapted for use, particularly ingestion, by a companion animal. In optional embodiments of the present invention, the present compositions have a pH of less than about 7, less than about 6, less than about 5, less than about 4, less than about 3.5, from about 2 to about 7, from about 2.5 to about 5, from about 2.5 to about 4, or from about 2.5 to about 3.5. Those compositions having a pH of less than about 3.5 are particularly preferred, as these compositions may not require refrigeration upon exposure to air such to provide shelf-stability over time and may not require aseptic packaging processes.

If necessary, the present compositions may comprise one or more acidulants in order to reach, and maintain, the desired pH. Acidity can be adjusted to and maintained within the requisite range by known and conventional methods, e.g., the use of one or more acidulants.

Organic as well as inorganic edible acids may be used to adjust the pH of the compositions. The acids can be present in their undissociated form or, alternatively, as their respective salts, for example, potassium or sodium hydrogen phosphate, potassium or sodium dihydrogen phosphate salts. Illustrative acids are edible organic acids which include citric acid, malic acid, fumaric acid, adipic acid, phosphoric acid, gluconic acid, tartaric acid, ascorbic acid, acetic acid, phosphoric acid or mixtures thereof.

The amount of edible acid utilized will, of course, be dependent at least in part upon desired acidity. As an example, the compositions may comprise from about 0.01% to about 5% edible acid, from about 0.1% to about 4% edible acid, from about 0.5% to about 3% edible acid, or from about 0.7% to about 2% edible acid, all by weight of the composition.

Omega-3-Fatty Acids

One or more omega-3-fatty acids may be added to the present compositions. The omega-3-fatty acid optionally utilized herein may be any omega-3-fatty acid or combination of omega-3-fatty acids. Non-limiting examples of omega-3-fatty acids which are suitable for use herein include eicosapentaenoic acid (also known as EPA), docosahexaenoic acid (also known as DHA), and mixtures thereof. Omega-3-fatty acids are often sourced from marine (fish) sources, including menhaden (a herring-like fish), or other sources such as flax.

Nutrients

The compositions herein may optionally, but preferably, be fortified further with one or more nutrients, especially one or more vitamins and/or minerals. Non-limiting examples of such vitamins and minerals, include niacin, thiamin, folic acid, pantothenic acid, biotin, vitamin A (including vitamin A (retinol), β-carotene, retinol palmitate, or retinol acetate), vitamin C, vitamin $B_2$, vitamin $B_3$, vitamin $B_6$, vitamin $B_{12}$, vitamin D, vitamin E, vitamin K, iron, zinc, copper, phosphorous, iodine, chromium, molybdenum, fluoride, calcium, manganese, magnesium, or boron.

Preservatives

One or more preservatives may additionally be utilized herein. Preferred preservatives include, for example, sorbate, benzoate, and polyphosphate preservatives. Preservatives may be avoided wherein the pH is manipulated to levels which are less than about 3.5.

Thickeners and Bulking Agents

The compositions according to the present invention may optionally further comprise one or more thickeners, including xanthan gum, carboxymethylcellulose, carboxyethylcellulose, hydroxypropylcellulose, methylcellulose, microcrystalline cellulose, starches, dextrins, fermented whey, tofu, maltodextrins, propylene glycol alginate, gellan gum, guar gum, pectin, tragacanth gum, gum acacia, locust bean gum, gum arabic, gelatin, as well as mixtures of these thickeners. Some of these thickeners may also be utilized as a fermentable fiber source.

Emulsifiers and Oils

One or more emulsifiers and/or oils may also be included in the present compositions for texture and opacity purposes. Typical emulsifiers and oils useful herein include, for example, mono-di glycerides, lecithin, pulp, cottonseed oil, and vegetable oil.

Vegetables

Optionally one or more vegetables may be included in the present compositions. Examples of such vegetables include celery, potato, tomato, pea, carrot, and the like. Vegetables may be dehydrated vegetables which are minced, diced, or otherwise prepared such that the particle size is controlled as desired.

Kits of the Present Invention

The present invention further relates to kits comprising the foregoing compositions and information, such that the consumer (including companion animal guardian, breeder, veterinarian, or the like) will readily comprehend benefits of the present compositions. In particular, the kits comprise:
  (a) a composition described herein; and
  (b) information selected from the group consisting of:
    (i) that the composition is adapted for use by a companion animal;
    (ii) that the composition is useful for enhancing gastrointestinal health;
    (iii) that the composition is useful for improving the fecal odor of the feces of a companion animal; and
    (iv) combinations thereof.

The kits of the present invention may comprise one or more compositions together with information which informs a user of the kit, by words, pictures, and/or the like, that use of the kit is useful for enhancement of gastrointestinal health of the companion animal, or that the composition is adapted for use by a companion animal. Such information need not utilize the actual terms used herein, for example, "gastrointestinal", "companion", or "adapted for use", but rather use of words or terms, pictures, symbols, and the like conveying the same or similar meaning are contemplated within the scope of this invention.

In a particularly preferred embodiment, the information is printed on a container holding the composition, e.g., a bottle. These preferred kits may be in the form of one bottle containing the composition, or may be obtained as a plurality of bottles each containing the composition. For example, the kits may be obtained as one bottle, or cases of four, six, seven or eight bottles co-packaged together. Each container may hold a variety of quantities of composition; for example, the container may contain a single dose or multiple doses of the composition.

Methods of the Present Invention

The methods of the present invention comprise orally administering (i.e., through ingestion) a composition of the present invention to a companion animal to provide improvement in gastrointestinal health and/or improvement in the fecal odor of the feces of the companion animal, as applicable. In one embodiment herein, the enhancement of gastrointestinal health may include any one or more of the following benefits: therapeutically relieving the symptoms of, or prevention of, gastrointestinal inflammatory disorders, inflammatory bowel disease, diarrhea or loose stools; otherwise improving fecal quality; weight loss associated with diarrhea or loose stools; treatment of small intestine bacterial overgrowth; or manipulation of levels of bacteria including improving levels of beneficial bacteria relative to harmful bacteria and/or decreasing pathogenic bacteria. Moreover, ancillary benefits to improvement in the fecal odor of the feces of the companion animal include removal of putrefactive substances which are known to promote, either directly or indirectly, carcinogenic effects in the mammalian system. Therefore, reducing pro-carcinogenic substances or effects, specifically reducing risk of cancer, is a useful benefit herein. Various methods of analysis directed to these benefits are described herein below.

The compositions of the present invention are most preferably ingested by companion animals. The compositions may be ingested as a supplement to normal dietetic requirements.

As used herein, the term "orally administering" with respect to the companion animal means that the animal ingests or a human is directed to feed, or does feed, the animal one or more compositions herein. Wherein the human is directed to feed the composition, such direction may be that which instructs and/or informs the human that use of the composition may and/or will provide the referenced benefit, for example, an enhanced gastrointestinal health benefit. For example, such direction may be oral direction (e.g., through oral instruction from, for example, a veterinarian or other health professional), radio or television media (i.e., advertisement), or written direction (e.g., through written direction from, for example, a veterinarian or other health professional (e.g., scripts), sales professional or organization (e.g., through, for example, marketing brochures, pamphlets, or other instructive paraphernalia), written media (e.g., internet, electronic mail, or other computer-related media)), and/or packaging associated with the composition (e.g., a label present on a container holding the composition). As used herein, "written" means through words, pictures, symbols, and/or other visible descriptors. Such information need not utilize the actual words used herein, for example, "gastrointestinal", "companion", or "adapted for use", but rather use of words, pictures, symbols, and the like conveying the same or similar meaning are contemplated within the scope of this invention.

The compositions described herein may be used as a supplement to ordinary dietetic requirements, or may be nutritionally balanced for those companion animals which have difficulty ingesting solid foods. Administration may be on an as-needed or as-desired basis, for example, once-monthly, once-weekly, or daily (including multiple times daily, or with each feeding). When utilized as a supplement to ordinary dietetic requirements, the composition may be administered directly to the companion animal or otherwise contacted with or admixed with companion animal food. The amount of composition utilized may be dependent on a variety of factors, including the quality of gastrointestinal health of the animal, preference of the animal as determined by the guardian of the animal or other person administering the composition, the quality of the companion animal food, and size or breed or the companion animal.

Methods of Analysis

The present compositions may be utilized to enhance the gastrointestinal health of the companion animal or improve fecal odor of the feces of the companion animal. Various methods of demonstrating such enhancements or improvements are well-known to those of ordinary skill in the art. As examples, the following provides illustrations of certain methods which may be used. These methods are not intended to limit the scope of the invention.

Methods of Enhancing Gastrointestinal Health:

Methods of measuring enhancements in gastrointestinal health of a companion animal will be well-known to those having ordinary skill in the art. An illustrative example of making such measurements is set forth in U.S. Pat. No. 5,952,033, which follows the general method described above with respect to measurement of fecal odor, with the following modifications: The levels of short chain fatty acids in the fecal matter are determined by gas chromatograph. The results indicate that administration of the test food results in increased short chain fatty acid concentrations relative to administration of the control food, which is believed to contribute to improved gastrointestinal health.

Additionally or alternatively, the compositions herein may be measured by their ability to reduce the amount of harmful bacteria in the small intestine (also referenced as treating small intestinal bacterial overgrowth, or IBO). Such methods are described in Reinhart, U.S. Pat. No. 5,776,524 (1998).

Additionally or alternatively, as one of ordinary skill in the art will recognize, fecal matter quality may also be indicative of gastrointestinal health. The treatment or prevention of gastrointestinal infection, including diarrhoea, in companion animals may be measured using stool scores. Stools scores may be recorded daily according to the following guidelines and control and test groups compared before and after administering the compositions according to the present invention.

Score: 5 Extremely Dry

This stool is hard and does not stick to surfaces. Stool will roll when pushed. No indentations are made when stool is picked up. Stool is often defecated in groups of individual stools instead of one complete unit. The stool maintains original shape after collection.

Score: 4 Firm (Ideal Stool)

This stool is firm, well shaped, and cylindrical. This stool does not break apart easily when picked up. This stool may leave residue on surfaces and gloves. This stool is often defecated as one unit. The stool maintains original shape after collection.

Score: 3 Soft, with Shape

This stool is soft, however there are definite shapes. This stool will break apart easily and will definitely leave residue on surfaces and gloves. The stool often loses original shape after collection. This stool is often present with another score but can comprise whole stool sample.

Score: 2 Soft, without Shape

This stool is soft and will have no cylindrical shape. The shape often associated with a "2" is a "cow patty" shape. This stool will lose the original shape when collected and will definitely leave residue on surfaces and gloves. This stool score is often present with another score but can comprise the whole stool sample. This stool sample may spread over an area of several inches.

Score: 1 Liquid

This stool score will always resemble liquid and there may or may not be particulate matter present. This stool will often be defecated in groups of piles instead of one complete unit. Mucous is often present with this stool sample. This stool sample is very difficult to collect and residue is always left on surfaces and gloves. This stool sample may spread over an area of several inches.

In addition, other observations are also recorded, including: blood in stool; foreign object in stool; or mucous in stool.

Furthermore, the enhancement of gastrointestinal health in companion animals may comprise improving microbial ecology of companion animals. Improving the microbial ecology of companion animals preferably comprises reducing the levels of pathogenic bacteria in the feces of companion animals. The levels of pathogenic bacteria present in the feces of companion animals may be enumerated using the standard plate count method known to those skilled in the art. More preferably, the pathogenic bacteria are selected from the group consisting of *Clostridia, Escherichia, Salmonella, Bacteriodes* and mixtures thereof. Non-limiting examples of suitable strains of pathogenic bacteria include *B. fragilis, C. perfringens, C. difficile, Eschericia coli, Salmonella typhimurium* and mixtures thereof.

Improvement of Fecal Odor of the Feces of a Companion Animal:

Methods of measuring improvement of fecal odor of the feces of a companion animal will be well-known to those having ordinary skill in the art. An illustrative example of making such measurements is set forth in U.S. Pat. No. 5,952,033, which generally instructs as follows: A trial is conduct using a defined number of dogs. The control food is provided, wherein the control food is a commercially available dry dog food (which is nutritionally balanced) which is devoid of short chain oligofructose. A test food is provided which corresponds to the control food except that it includes from about 0.01% to about 0.2% of short chain oligofructose, by weight of the food, as described herein. Half of the dogs are fed the control food and the remaining half are fed the test food. Fecal samples are collected from each dog, heated for 2 hours at 30° C., and the compounds released are trapped on a Tenax tube, or equivalent. The trapped compounds are desorbed on a gas chromatograph. The levels of dimethylsulfide, dimethldisulfide, and dimethyltrisulfide are determined for each of the control and test foods. The results indicate that administration of the test food results in improved fecal odor relative to administration of the control food, as measured by decreases in the levels of dimethylsulfide, dimethldisulfide, and dimethyltrisulfide, which are believed to cause unpleasant odor.

Methods of Making

The presently described compositions are made according to methods which will be well known by the ordinarily skilled artisan. To illustrate, the compositions of the present invention may be prepared by dissolving, dispersing, or otherwise mixing all components singularly or in suitable combinations together, and in water where appropriate, agitating with a mechanical stirrer until all of the ingredients have been solubilized or adequately dispersed.

An example of a process which may be utilized to manufacture the present compositions may be adapted in accordance with the following general disclosure (all non-requisite components are set forth to demonstrate illustrative components):

1. Add water to tank.
2. Add any antioxidant to animal fat and mix well.
3. Under constant agitation, add liquid fructooligosaccharide and animal fat to the water. Mix thoroughly.
4. Pre-mix any animal solids, broth powder, xanthan gum, vitamin and mineral pre-mixes, and yeast to form a "meat pre-mix".
5. Under constant agitation, slowly add meat pre-mix and mix well to ensure powder is well dispersed. (Alternatively, the xantham gum could be added using well-known high shear techniques to ensure adequate dispersion of the gum. Other solids can also be added individually with constant mixing.)
6. Pass product batch through a disintegrator or other high shear dispersing equipment to ensure all powders (particularly the gum) is well dispersed and no large clumps of powder remain.
7. Pre-mix vegetables ingredients into a "vegetable pre-mix", including beet pulp, flax and vegetables.
8. Slowly add vegetable pre-mix to batch under constant agitation. Mix well.
9. Heat batch to 195° F. and hold for 5 minutes.
10. Cool batch to at least 130° F.
11. Add ½ of predicted level of phosphoric acid and mix well.
12. Add potassium sorbate, mix well.
13. Add flavors and mix.
14. Add additional phosphoric acid to achieve the target pH. Mix well.

EXAMPLES

The following are non-limiting examples of the present compositions which are prepared utilizing conventional methods. The following examples are provided to illustrate the invention and are not intended to limit the scope thereof in any manner.

Example 1

A beef-flavor gravy composition is prepared by combining the following components in a conventional manner:

| Component | Wt % |
| --- | --- |
| Fructooligosaccharide | 5.3 |
| Chicken Fat | 3.0 |
| Spray-Dried Beef Particles and Broth | 3.0 |
| Xanthan Gum | 0.5 |
| Flax Seed | 0.2 |
| Vegetables | 0.2 |
| Vitamins | 0.06 |
| Minerals | 0.04 |
| Phosphoric Acid | 0.95 |
| Beef Flavor | 0.1 |
| Water | Remainder |

One fluid ounce of the gravy composition is admixed with one-half cup of standard dog kibble diet daily prior to feeding to a dog. Amounts of the gravy composition are determined as desired by the guardian of the dog.

Example 2

A chicken-flavor gravy composition is prepared by combining the following components in a conventional manner:

| Component | Wt % |
| --- | --- |
| Short Chain Oligofructose (NUTRAFLORA, commercially available from GTC Nutrition, Golden, CO., U.S.A.) | 5.3 |
| Chicken Fat | 3.0 |
| Spray-Dried Chicken Particles and Broth | 3.0 |
| Beet Pulp | 0.4 |
| Xanthan Gum | 0.5 |
| Flax Seed | 0.15 |
| Vegetables | 0.2 |
| Vitamins | 0.06 |
| Minerals | 0.04 |
| Phosphoric Acid | 0.95 |
| Chicken Flavor | 0.53 |
| Water | Remainder |

Two fluid ounces of the gravy composition is admixed with one-half cup of standard dog kibble diet daily prior to feeding to a dog.

Example 3

The following illustrates how to use the present compositions. Twenty-four dogs having intestinal bacterial overgrowth are used to determine the effects of the composition according to Example 1 on the dog gastrointestinal system. The dogs are of age ranging from 12 months to 24 months old. The dogs are fed an initial diet (Diet A) for two months. Diet A contains no fermentable fiber, but each feeding contains 10 ounces of kibble containing chicken by-product meal, corn, chicken fat, rice, Brewers yeast, egg, nutrients, and corn starch, which is admixed with 2 ounces of a gravy in accordance with Example 1 except that water substitutes for the fructooligosaccharide and beet pulp. Intestinal juice and mucosal tissue from the dogs is sampled and cultured at conclusion of feeding Diet A. Twenty-eight days afterwards, the dogs are fed Diet B, which is same kibble utilized in Diet A but mixed with the composition according to Example 1. Intestinal juice, mucosal tissue, and fresh fecal samples are re-sampled 6 weeks after starting Diet B. The intestinal juice and mucosal tissue are sampled for aerobic and anaerobic bacteria. The dogs ingesting Diet B show significantly fewer aerobic and anaerobic bacteria in the intestinal juice and mucosa, and beneficical (*Bifidobacteria, Lactobacilli, Eubacteria*) and pathogenic (*B. fragilis, C. perfringens, C. difficile, Eschericia coli*) in the intestinal juice, mucosa, and fecal samples relative to sampling occurring upon ingestion of Diet A.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A method of enhancing the gastrointestinal health of a companion animal in need thereof, comprising orally administering to the companion animal an effective amount of a composition comprising at least about 0.25% of fermentable fiber by weight of the composition, wherein the fermentable fiber comprises a short chain oligofructose comprising from about 30% to about 40% 1-kestose, from about 50% to about 60% nystose, and from about 5% to about 15% 1F-beta-fructofuranosylnystose, by weight of the short chain oligofructose; and wherein the composition is a supplement.

2. The method of claim 1, wherein the fermentable fiber further comprises a fiber selected from beet pulp, gum Arabic, gum talha, psyllium, rice bran, carob bean gum, citrus pulp, pectin, fructooligosaccharide, mannanoligofructose, soy fiber, arabinogalactan, galactooligosaccharide, arabinoxylan, or mixtures thereof.

3. The method of claim 2, wherein the composition is a liquid.

4. The method of claim 2, wherein the composition is a gravy.

5. The method of claim 2, wherein the oral administration is at least once daily.

6. The method of claim 2, wherein the composition is contacted with companion animal food prior to oral administration.

7. The method of claim 2, wherein the composition is admixed with companion animal food prior to oral administration.

8. The method of claim 1, wherein the fermentable fiber further comprises beet pulp.

9. The method of claim 8, wherein the composition is a liquid.

10. The method of claim 8, wherein the composition is a gravy.

11. The method of claim 8, wherein the oral administration is at least once daily.

12. The method of claim 8, wherein the composition is contacted with companion animal food prior to oral administration.

13. The method of claim 8, wherein the composition is admixed with companion animal food prior to oral administration.

14. A method of improving the fecal odor of the feces of a companion animal in need thereof, comprising orally administering to the companion animal an effective amount of a composition comprising at least about 0.25% of fermentable fiber by weight of the composition, wherein the fermentable fiber comprises a short chain oligofructose comprising from about 30% to about 40% 1-kestose, from about 50% to about 60% nystose, and from about 5% to about 15% 1F-beta-fructofuranosylnystose, by weight of the short chain oligofructose; and wherein the composition is a supplement.

15. The method of claim 14, wherein the fermentable fiber further comprises a fiber selected from beet pulp, gum Arabic, gum talha, psyllium, rice bran, carob bean gum, citrus pulp, pectin, fructooligosaccharide, mannanoligofructose, soy fiber, arabinogalactan, galactooligosaccharide, arabinoxylan, or mixtures thereof.

16. The method of claim 1, wherein the fermentable fiber consists of beet pulp and the short chain oligofructose, and wherein the composition is a gravy.

17. The method of claim 8, wherein the fermentable fiber consists of beet pulp and the short chain oligofructose and the composition is a gravy.

* * * * *